United States Patent [19]

Stuetz

[11] Patent Number: 4,755,534
[45] Date of Patent: Jul. 5, 1988

[54] PROPENYLAMINES, PHARMACEUTICAL COMPOSITIONS CONTAINING THEM AND THEIR USE AS PHARMACEUTICALS

[75] Inventor: Anton Stuetz, Maria Enzersdorf, Austria

[73] Assignee: Sandoz Ltd., Basel, Switzerland

[21] Appl. No.: 646,724

[22] Filed: Sep. 4, 1984

Related U.S. Application Data

[63] Continuation of Ser. No. 233,559, Feb. 11, 1981, abandoned, which is a continuation-in-part of Ser. No. 180,207, Aug. 21, 1980, abandoned.

[30] Foreign Application Priority Data

Aug. 22, 1979 [CH] Switzerland ............... 7656/79

[51] Int. Cl.$^4$ ............... A61K 31/135; C07C 87/28
[52] U.S. Cl. ............... 514/655; 564/387
[58] Field of Search ............... 564/387; 280/501.1; 514/645, 657, 658

[56] References Cited

U.S. PATENT DOCUMENTS 3,270,056  8/1966  Martin et al. ............ 564/387 X
4,282,251  8/1981  Berney ............ 564/387 X
4,680,291  7/1987  Hamberger et al. ............ 564/387 X

FOREIGN PATENT DOCUMENTS 0000896  3/1979  European Pat. Off. ............ 564/387

Primary Examiner—Robert V. Hines
Attorney, Agent, or Firm—Gerald D. Sharkin; Robert S. Honor; Thomas O. McGovern

[57] ABSTRACT

A compound of the formula:

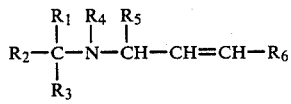

wherein the double bond is in the trans configuration and $R_1$ is a radical of formula IIa,

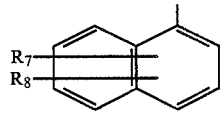

$R_2$, $R_3$, $R_5$, $R_7$ and $R_8$ are each hydrogen,
$R_4$ is methyl, and
$R_6$ is a radical of formula IIIa

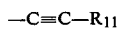

where $R_{11}$ is n-butyl, tertiary butyl or phenyl or a chemotherapeutically acceptable acid addition salt thereof; processes for their production, their use as pharmaceuticals and pharmaceutical compositions containing them.

7 Claims, No Drawings

PROPENYLAMINES, PHARMACEUTICAL COMPOSITIONS CONTAINING THEM AND THEIR USE AS PHARMACEUTICALS

This is a continuation of application Ser. No. 233,559, filed Feb. 11, 1981, and now abandoned which in turn is a continuation-in-part of application Ser. No. 180,207, filed Aug. 21, 1980, now abandoned.

This invention relates to propenylamines, processes for their production, pharmaceutical compositions containing them and their use as pharmaceuticals.

The invention provides compounds of formula I,

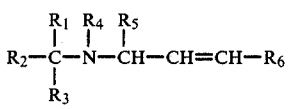     I wherein (a) $R_1$ represents a group of formula

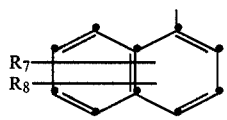     IIa

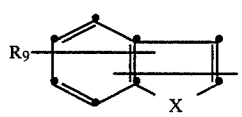     IIb

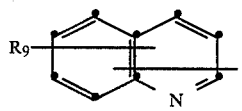     IIc

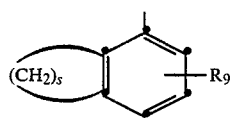     IId

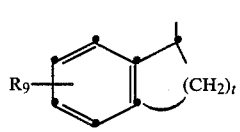     IIe

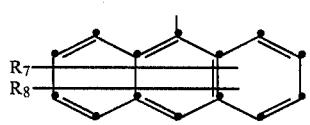     IIf or

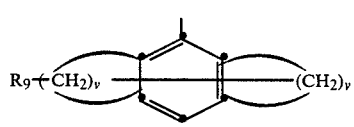     IIg and $R_2$ represents hydrogen or lower alkyl, or $R_1$ and $R_2$ together represent a group of formula

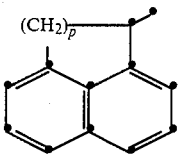     IIh

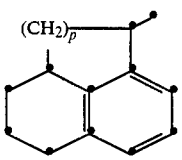     IIi whereby in the formulae IIa to IIi, $R_7$ and $R_8$ represent, independently, hydrogen, halogen, trifluoromethyl, hydroxy, nitro, lower alkyl or lower alkoxy, $R_9$ represents hydrogen, halogen, hydroxy, lower alkyl or lower alkoxy, X represents oxygen, sulphur, imino, lower alkyl imino or a radical of formula —$(CH_2)_r$—, p is 1, 2 or 3,
r is 1, 2 or 3,
s is 3, 4 or 5,
t is 2, 3 or 4, and
v is 3, 4, 5 or 6;

$R_3$ and $R_5$ represent, independently, hydrogen or lower alkyl, and $R_4$ represents $C_{1-6}$alkyl or $C_{3-8}$cycloalkyl-$(C_{1-6})$-alkyl; and $R_6$ represents a group of formula —C≡C—$R_{11}$    IIIa     $-\underset{R_{11}}{C}=CH_2$    IIIb or

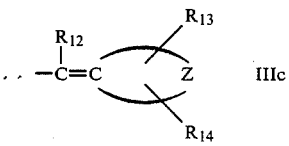     IIIc wherein $R_{11}$ represents hydrogen, optionally α-hydroxy substituted alkyl; alkenyl, alkynyl, cycloalkyl, cycloalkylalkyl, phenyl, phenalkyl or thienyl, $R_{12}$, $R_{13}$ and $R_{14}$ represent, independently, hydrogen or lower alkyl, and

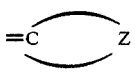

represents a $C_{5-8}$ cycloalkylidene radical optionally containing a double bond; or (b) $R_1$ represents a group of formula IIa to IIg as defined under (a), $R_2$ represents hydrogen or lower alkyl, $R_3$ and $R_4$ together form a group —$(CH_2)_u$—, wherein u is an integer of 1 to 8, and $R_5$ and $R_6$ have the meanings given under (a).

Any lower alkyl or lower alkoxy radical has preferably 1 to 4 carbon atoms, especially 2 or 1 carbon atoms. Unless otherwise stated alkyl moieties preferably have 1 to 12 carbon atoms especially 2 to 8 carbon atoms, particularly 2 to 6 carbon atoms and most preferably 3 to 5 carbon atoms and if bridging 1 to 4 particularly 1 or 2 carbon atoms. Any alkenyl or alkynyl radical has preferably 3 to 6 carbon atoms, especially 3 to 4 carbon atoms, e.g. allyl, propenyl or propynyl. Such alkyl, alkoxy, alkenyl and alkinyl groups can be straight-chain or branched. A preferred cycloalkylidene radical is cyclohexylidene. The term cycloalkyl is to be understood as including polycyclo groups such as bornyl or adamantyl but is preferably cyclohexyl or cyclopentyl.

Conveniently $R_7$ and $R_8$ are identical and are both hydrogen. Conveniently $R_9$ is hydrogen or halogen. In IIb and IIc the bond to the carbon atom to which $R_2$ and $R_3$ are attached is conveniently attached meta to X and para to the ring nitrogen, respectively. X is conveniently sulphur, imino or lower alkylamino. $R_1$ is preferably a radical of formula IIb, IIc or IId, or especially IIa. $R_2$ is preferably hydrogen. $R_3$ is preferably hydrogen and $R_4$ is conveniently alkyl. $R_5$ is conveniently hydrogen.

The values of p, r, s, t, u and v are conveniently chosen to produce a seven- preferably a five- or six-membered ring.

The double bond between $R_6$ and the nitrogen atom preferably has the trans-configuration.

Halogen stands for fluorine, chlorine or bromine, preferably chlorine or bromine.

The present invention also provides a process for the production of a compound of formula I, which comprises (a) when $R_6$ represents a group of formula IIIa, as defined above, (compound Ia), reacting a compound of formula IV,

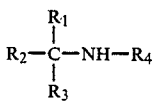          IV wherein
$R_1$ to $R_4$ are as defined above, with a conpound of formula V,

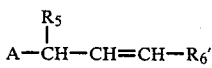          V wherein
A is a leaving group, $R_5$ is as defined above, and
$R_6'$ stands for a group of formula IIIa, as defined above, or (b) when $R_6$ represents a group of formula IIIa, wherein $R_{11}$ represents α-hydroxyalkyl (compounds Ib), reacting a metalated compound of formula Ic,

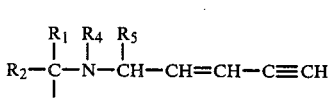          Ic wherein $R_1$ to $R_5$ are as defined above, with a carbonyl compound of formula VII,

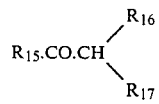          VII wherein $R_{15}$, $R_{16}$ and $R_{17}$ represent independently hydrogen or lower alkyl, or (c) when the double bond between $R_6$ and the nitrogen atom is in trans configuration (compounds Id) reducing a compound of formula VIII,

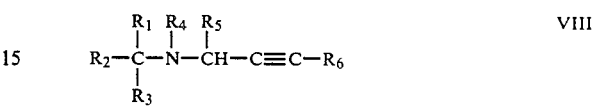          VIII wherein $R_1$ to $R_6$ are as defined above, with diisobutylaluminumhydride, or (d) when $R_6$ represents a group of IIIb or IIIc as defined above or a group of formula IIId,

          IIId wherein $R_{15}$, $R_{16}$ and $R_{17}$ are as defined above (compounds Ie) splitting off water from a compound of formula

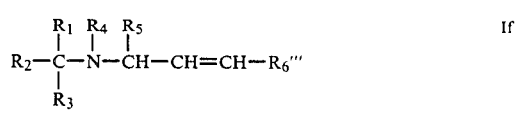          If wherein
$R_1$ to $R_5$ are as defined above, and
$R_6'''$ represents a group of formula IIIe, IIIf, or IIIg,

          IIIe

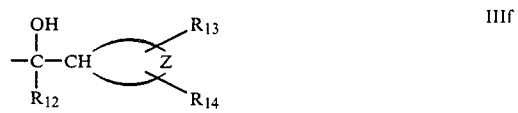          IIIf

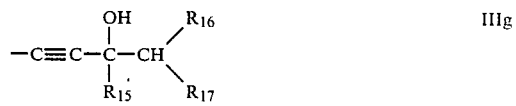          IIIg wherein
$R_{11}$ to $R_{17}$ and Z are as defined above, or (e) when $R_3$ represents hydrogen or lower alkyl and $R_4$ represents $C_{1-6}$alkyl or $C_{3-8}$cycloalkyl-($C_{1-6}$)-alkyl (compounds Ig), introducing the group $R_4'$ into a compound of formula IX,

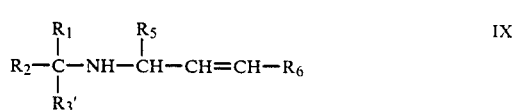          IX wherein $R_1$, $R_2$, $R_5$ and $R_6$ are as defined above, $R_3'$ represents hydrogen or lower alkyl, and $R_4'$ represents $C_{1-6}$alkyl or $C_{3-8}$cycloalkyl-$(C_{1-6})$-alkyl.

Process (a) may be effected in conventional manner for the production of tertiary amines by condensation from analogous starting materials. The process may be effected in an inert solvent such as a lower alkanol, e.g. ethanol, optionally in aqueous admixture, an aromatic hydrocarbon solvent, e.g. benzene or toluene, a cyclic ether, e.g. dioxane or a carboxylic acid dialkylamide solvent, e.g. dimethylformamide. The reaction temperature is conveniently from room temperature to the boiling temperature of the reaction mixture, preferably room temperature. The reaction is conveniently effected in the presence of an acid binding agent, such as an alkali metal carbonate, e.g. sodium carbonate. The leaving group A is conveniently iodine or preferably chlorine or bromine, or an organic sulphonyloxy group having 1 to 10 carbon atoms, e.g. alkylsulphonyloxy, preferably having 1 to 4 carbon atoms such as mesyloxy, or alkylphenylsulphonyloxy preferably having 7 to 10 carbon atoms such as tosyloxy.

Process (b) may be effected in conventional manner, for example by metalating the compound of formula Ic, e.g. with butyllithium in an inert solvent such as an ether e.g. tetrahydrofuran and subsequently reacting the metalated compound of formula Ic, thus obtained, preferably without isolation with a compound of formula VII.

The reduction with diisobutylaluminium hydride (DIBAH) according to process (c) is preferably carried out in an inert solvent e.g. in an aromatic hydrocarbon such as toluene or benzene and at room temperature or raised temperature e.g. 35° to 40° C.

The splitting-off of water according to process (d) can be carried out with a suitable agent such as an inorganic acid, e.g. hydrochloric or sulphuric acid, an organic acid, e.g. methanesulphonic acid, bezenesulphonic acid or p-toleuensulphonic acid or an inorganic or organic acid anhydride or -halide e.e. $POCl_3$ in an inert solvent. An excess of an acid halide if used can act as reaction medium whereby the reaction is carried out in the presence of an acid binding agent such as a tertiary amine, e.g. a trialkylamine or pyridine. Reaction temperatures vary according to reaction conditions and lie for example between $-10°$ and 180° C. The splitting-off of water can also be carried out with the help of polyphosphoric acid at temperatures between 80° and 120° C. whereby inorganic acids such as phosphoric acid, organic acids such as acetic acid or an excess of polyphosphoric acid can serve as solvent.

Process (e) may be effected in manner conventional for the "alkylation" or secondary amines (the term "alkylation" being used here to denote introduction of any of the hydrocarbyl groups $R_4$), for example by direct "alkylation" with an "alkylating" agent, for example a halide or sulphate, or by reductive alkylation, in particular by reaction with an appropriate aldehyde and subsequent or simultaneous reduction,. Reductive "alkylation" is suitably effected by reacting a compound of formula IX in an inert organic solvent, such as a lower alkanol, e.g. methanol, and at an elevated temperature, in particular at the boiling temperature of the reaction mixture with the corresponding aldehyde. The subsequent reduction may be effected with, for example, a complex metal hydride reducing agent, e.g. $NaBH_4$ or $NaCNBH_3$. The reduction may also be effected simultaneously to the alkylation, for example by use of formic acid which may serve both as reducing agent and as a reaction medium. The reaction is preferably carried out at raised temperature, in particular at the boiling point of the reaction mixture.

Free base forms of the compounds of formula I may be converted into salt forms and vice versa. Suitable acid addition salts are e.g. hydrochloride, hydrogen fumarate or naphthaline-1,5-disulphonate.

The compounds of the formula I and their intermediates can be obtained in the form of isomeric mixtures of the various cis/trans isomers which can be separated according to established methods. Alternatively, isomers of the compounds can be obtained by using the appropriate isomer of the starting material. Unless otherwise stated the compounds are always to be understood as being mixtures of these isomers.

The starting materials of formula IV are in part new and can be prepared by reacting in conventional manner a compound of formula X,

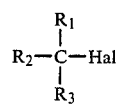   X with a compound of formula XI,

   XI wherein in the formulae X and XI $R_1$ to $R_4$ are as defined above and Hal stands for halogen.

The starting materials of formula V are in part new and can be prepared by reacting a compound of formula XII,

   XII according to the following scheme

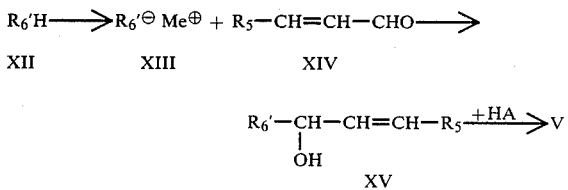

whereby $R_6'$, $R_5$ and A are as defined above and $Me^\oplus$ represents a metal cation.

The starting materials of formula VIII are new and can be prepared (a') by subjecting a compound of formula IV, defined above, and compounds of formulae XVI and XVII

   XVI and

   XVII to a Mannich reaction or (b') in the case when $R_6$ represents a group of formula IIIa as defined above by reacting a compound of formula IV as defined above with a compound of formula XVIII

   XVIII to give a compound of formula XIX,

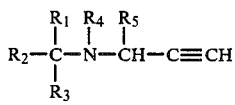   XIX and subjecting this to a Cadiot-Chodkiewicz coupling reaction with Cu+ and a compound of formula XX,

   XX or (c') when $R_6$ represents a group of formula IIIb as defined above splitting off water from a compound of formula XXI,

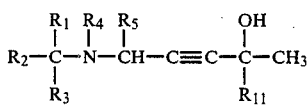   XXI whereby in the formulae XVI to XXI $R_1$ to $R_6$, $R_6'$, $R_{11}$, A and Hal are as defined above.

The starting materials of formula IX are new and can be prepared for example by reacting a compound of formula XXII,

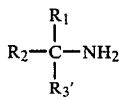   XXII with a compound of formula XXIII

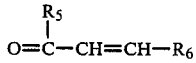   XXIII to give a compound of formula XXIV

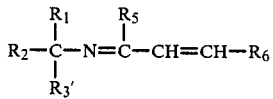   XXIV and reducing the e.g. with a complex hydride such as NaBH$_4$, whereby in the formulae XXII to XXIV $R_1$, $R_2$, $R_3'$, $R_5$ and $R_6$ are as defined above.

Compounds of formula XXI can be prepared (a'') by subjecting a compound of formula IV as defined above, a compound of formula XVII as defined above, and a compound of formula XXV,

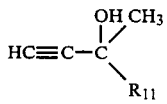   XXV to a Mannich reaction, or (b'') metalating a compound of formula XIX, as defined above, and reacting the metal compound thus obtained with a carbonyl compound of formula XXVI, $CH_3.CO.R_{11}$   XXVI whereby in the formulae XXV and XXVI $R_{11}$ is as defined above.

The compounds of formulae IVa and IVb

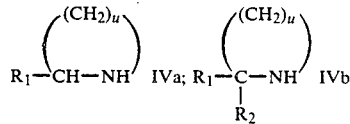   IVa; IVb can be prepared according to the following scheme

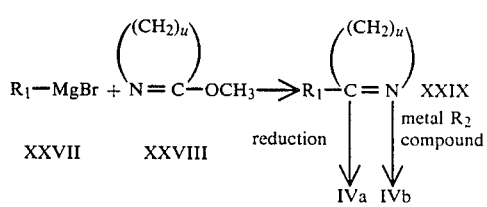   XXIX

XXVII   XXVIII   reduction   metal $R_2$ compound

IVa   IVb whereby in the formulae IVa, IVb and XXVII to XXIX $R_1$, $R_2$ and u are as defined above.

The starting materials of formula If wherein $R_6'''$ represents a group of formula IIIe or IIIf as defined above are new and can be prepared by reduction with LiAlH$_4$ of a compound of formula XXIa,

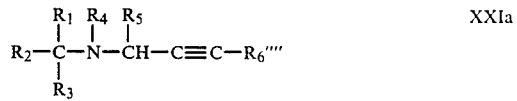   XXIa wherein $R_1$ to $R_5$ are as defined above and $R_6''''$ represents a group of formula IIIe or IIIf as defined above.

Compounds of formula XX are in part new and can be prepared by reacting a compound of formula XII, as defined above, with butyllithium and a halogen.

The new compounds of formulae IV, V, VIII, IX XX and If also form part of the invention. The remaining intermediate compounds are either known or can be prepared according to known methods or as hereinbefore described.

The compounds of formula I are useful because they possess chemotherapeutic activity. In particular, they are useful as antimycotic agents, as indicated in vitro in various families and types of mycetes, including Trichophyton spp, Aspergillus spp, Microsporum spp and Sporotrychium schenkii and Candida spp at concentrations of, for example 0.01 to 100 μg/ml, and in vivo in the experimental skin mycosis model in guinea pigs. In this model, guinea pigs are infected by subcutaneous applications of Trichophyton Quinckeanum. The test substance is administered daily for 7 days beginning 24 hours after the infection either by local application by rubbing the test substance (taken up in polyethylene glycol) on the skin surface, or perorally or sub-cutaneously, the test substance being administered as a suspension. The activity is shown on local application at concentrations of for example 0.01 to 5%. The oral activity is shown in vivo in the guinea pig—Trichophytosis model at dosages of, for example 2 to 70 mg/kg.

For the above-mentioned use, the dose administered will of course vary depending on the compound employed, mode of administration and treatment desired. However, in general, satisfactory results are obtained when administered at a daily dosage of from 1 to 100 mg/kg of animal body weight, conveniently given in divided doses two to four times daily, or in sustained release form. For the larger mammals, the corresponding daily dosages are in the range of from 70 to 2000 mg, and dosage forms suitable for oral administration comprise from 17.5 to 1000 mg. The invention therefore also concerns a method of treating diseases or infections caused by mycetes using a compound of formula I.

The compounds may be used in free base form or in the form of chemotherapeutically acceptable acid addition salts. Such salt forms exhibit the same order of activity as the free base forms. Suitable salt forms are e.g. hydrochloride, hydrogen fumarate or napththaline-1,5-disulphonate.

The compounds may be admixed with conventional chemotherapeutically acceptable diluents and carriers, and, optionally, other excipients and administered in such forms as tablets or capsules. The compounds may alternatively be administered topically in such conventional forms as ointments or creams or parenterally. The concentrations of the active substance will of course vary depending on the compound employed, the treatment desired and the nature of the form etc. In gereral, however, satisfactory results are obtained e.g. in topical application forms at concentrations of from 0.05 to 5, in particular 0.1 to 1 wt %.

Such compositions also form part of the invention.

Examples of preferred compound groups are (i) compounds of formula I wherein $R_6$ represents a group of formula IIIa wherein $R_{11}$ represents alkyl preferably $C_2$–$C_8$alkyl, more preferably $C_2$–$C_6$alkyl, most preferably $C_3$–$C_5$alkyl for example n- or in particular t-butyl;

(ii) compounds of formula I wherein $R_6$ represents a group of formula III wherein $R_{11}$ represents α-hydroxy substituted alkyl; alkenyl, alkynyl, cycloalkyl, cycloalkylalkyl, phenyl, phenalkyl or thienyl;

(iii) compounds of formula I wherein $R_{11}$ represents alkyl, alkenyl, alkynyl, cycloalkylalkyl, phenyl or phenalkyl and all other substituents are as defined under formula I;

(iv) compounds of formula I wherein (a)
$R_1$ represents a group of the formula IIa, IIb, IIe,
$R_2$ represents hydrogen,
$R_3$ represents hydrogen,
$R_4$ represents lower alkyl,
$R_5$ represents hydrogen or lower alkyl, or
$R_3$ and $R_4$ together form a group —$(CH_2)_u$— or
(b) wherein
$R_1$ and $R_2$ together represent a group of the formula IIh,
$R_3$ represents hydrogen,
$R_4$ represents lower alkyl,
$R_5$ represents lower alkyl and
$R_6$ is as hereinbefore defined,
whereby within these groups $R_6$ is preferably a group of formula IIIa as hereinbefore defined or as described under (i) or (ii) above and/or $R_1$ is preferably a group of formula IIa.

Preferred meanings of the substituents in the compounds of the formula I are such as set out hereinbefore.

Compounds of formula I are generally preferred wherein the double bond between $R_6$ and the nitrogen atom is in trans-configuration.

Particularly preferred individual compounds are:
N-methyl-N-(1-naphthylmethyl)-non-2(trans)-en-4-ynyl-1-amine and N-methyl-N-(1-naphthylmethyl)-6,6-dimethyl-hept-2(trans)-en-4-ynyl-1-amine, and their hydrochlorides.

The following Examples illustrate the invention whereby all temperatures are in degrees centigrade.

EXAMPLE 1 trans-N-(3-Benzo[b]thiophenemethyl)-N-methyl-non-2-en-4-ynyl-1-amine and
cis-N-(3-Benzo[b]thiophenemethyl)-N-methyl-non-2-en-4-ynyl-1-amine [process (a)]

12 g 1-Bromo-2-nonen-4-yne (cis/trans mixture) are added dropwise to a mixture of 10.5 g N-(3-Benzo[b]thiophenemethyl)-N-methylamine, 8.2 g $K_2CO_3$ and 100 ml dimethylformamide and stirred overnight. The reaction mixture is filtered and the solvent removed under vacuum. The residue is partitioned between ether and saturated aqueous $NaHCO_3$, the organic phase dried, concentrated under vacuum and chromatographed over kieselgel using toluene/ethylacetate 4:1 as eluant. The trans isomer is eluted first followed by the cis isomer. Both are oils.

EXAMPLE 2 trans-N-Methyl-N-(1-naphthylmethyl)-6-hydroxy-6-methyl-hept-2-en-4-ynyl-1-amine [process (b)]

10.7 ml of a 15% butyllithium solution in hexane are added dropwise to 3 g of trans N-methyl-N-(1-naphthylmethyl)pent-2-en-4-ynyl-1-amine in absolute tetrahydrofuran and reacted after 30 minutes with a solution of 1.79 g of acetone. The reaction mixture is stirred for 24 hours at room temperature, poured onto ice and extracted with chloroform. The organic phase is washed, dried and concentrated under vacuum. After chromatography over kieselgel (eluant toluene/ethyl acetate 4:1) the title compound is obtained as an oil.

EXAMPLE 3

(a)
trans-N-Methyl-N-(1-naphthylmethyl)-non-2-en-4-ynyl-1-amine [process (c)]

72 ml of a 1.2M solution of DIBAH in toluene are added dropwise to a solution of 5 g N-methyl-N-(1-naphthylmethyl)-2,4-nonadiynyl-1-amine in dry toluene and the resulting mixture stirred under protective gas overnight at 40° and then for 24 hours at room temperature.

The excess reagent is broken down with 2N NaOH under cooling and the reaction mixture extracted with ether. The organic phase is dried, concentrated under vacuum and chromatographed over kieselgel (eluant—toluene/ethylacetate 95:5). The title substance is isolated as an oil.

(b) Hydrochloride salt

The compound from (a) is converted to its hydrochloride in conventional manner e.g. by treating with 4N ethanolic HCl and melts after recrystallisation at 118°–121° C.

EXAMPLE 4

N-Methyl-N-(1-naphthylmethyl)-deca-2-(trans),6(cis)-dien-4-ynyl-1-amine 1 g trans-N-Methyl-N-(1-naphthylmethyl)-6-hydroxy-dec-2-en-4-ynyl--amine are refluxed under a water separator with 570 mg p-toluenesulphonic acid (monohydrate) in benzene. The mixture is cooled after 2 hours, the organic phase shaken a number of times with saturated aqueous NaHCO₃, dried and concentrated under vacuum. The residue is chromatographed over kieselgel (eluant—toluene/ethylacetate 9:1) to give the title product.

EXAMPLE 5

N-Methyl-N-(1-naphthylmethyl)-4-cyclohexyl-2-(trans)-4-pentadienyl-1-amine (A) and N-Methyl-N-(1-naphthylmethyl)-4-cyclohexylidenyl-2-(trans)-pentenyl-1-amine (B)

1 g N-Methyl-N-(1-naphthylmethyl)-4-hydroxy-4-cyclohexyl-2-pentenyl-1-amine is refluxed under a water separator with 570 mg p-toluenesulphonic acid (monohydrate) in benzene. The mixture is cooled after 2 hours, the organic phase shaken a number of times with saturated aqueous NaHCO₃, dried and concentrated under vacuum. The residue is chromatographed over kieselgel (eluant—toluene/ethyl acetate 9:1) to obtain first title product (A) followed by title product (B) as oils.

EXAMPLE 6 trans-N-Methyl-N-(1-naphthylmethyl)-4-cyclohexylidenyl-2-buten-yl-amine [process (e)]

3 g (1-Naphthylmethyl)amine and 2.86 g 4-cyclohexylidenyl-2-butenal are stirred in ether together with a 4 Å molecular sieve. The reaction mixture is filtered and concentrated under vacuum. The residue is taken up in methanol, treated with 800 mg NaBH₄ and stirred for 2 hours at room temperature.

The reaction mixture containing the secondary amine thus obtained is taken directly for reductive methylation. 8 ml 37% aqueous formaldehyde solution are added and refluxed for 1 hour. The mixture is then treated under ice-cooling with 3.6 g NaBH₄ and stirred for 16 hours at room temperature. The resulting mixture is concentrated under vacuum, the residue partitioned between saturated NaHCO₃ and ethyl acetate and the organic phase dried and concentrated. The title substance is obtained by chromatography over kieselgel (eluant—toluene/ethyl acetate 4:1) as an oil.

The following compounds of formula I can be obtained in an analogous manner.

TABLE I

| Example | R₁ | R₂ | R₃ | R₄ | R₅ | R₆ | Conf. | Physical data | Proc. |
|---------|----|----|----|----|-----|----|-------|---------------|-------|
| 7 | benzothiophene | H | H | CH₃ | H | —C≡C—(CH₂)₃—CH₃ | trans | oil | c, e |
| 8 | " | H | H | CH₃ | H | " | cis | oil | e |
| 9 | naphthyl | H | H | CH₃ | H | " | cis | oil | a, e |
| 10 | dihydronaphthyl (H) | H | H | CH₃ | H | " | trans | oil | a,c,e |
| 11 | " | H | H | CH₃ | H | " | cis | oil | a, e |
| 12 | benzofuran | H | H | CH₃ | H | " | trans | oil | a,c,e |
| 13 | " | H | H | CH₃ | H | " | cis | oil | a, e |
| 14 | naphthyl | H | H | CH₃ | H | —C≡CH | trans | mp (hydrochloride) 150–155° | a,c,e |
| 15 | " | | H | R₃ + R₄ + N | H | " | trans | mp (hydrochloride) 150–155° | a,c |
| 16 | " | H | H | CH₃ | H | —C≡C—C(CH₃)₃ | trans | m.p. (hydrochloride) | a,c,e |

TABLE I-continued

| Example | $R_1$ | $R_2$ | $R_3$ | $R_4$ | $R_5$ | $R_6$ | Conf. | Physical data | Proc. |
|---|---|---|---|---|---|---|---|---|---|
| | | | | | | | | 199–202° (crystal invertion above 135°) | |
| 17 | " | H | H | $CH_3$ | H | " | cis | oil | a, e |
| 18 | " | H | H | $CH_3$ | H | $-C{\equiv}C-C_6H_5$ | trans | oil | a,c,e |
| 19 | " | H | H | $CH_3$ | H | " | cis | oil | a, e |
| 20 | " | H | H | $CH_3$ | H | $-C{\equiv}C-CH(CH_3)(C_2H_5)$ | trans | m.p. (hydrochloride) 160–162° | a,c,e |
| 21 | " | H | H | $CH_3$ | H | " | cis | oil | a,e |
| 22 | " | H | H | $CH_3$ | H | $-C{\equiv}C-CH_2-CH(CH_3)_2$ | trans | m.p. (hydrochloride) 124–126° | a,c,e |
| 23 | " | H | H | $CH_3$ | H | " | cis | oil | a, e |
| 24 | " | H | H | $CH_3$ | H | $-C{\equiv}C-\text{(thienyl)}$ | trans | oil | a,c,e |
| 25 | " | H | H | $CH_3$ | H | $-C{\equiv}C-C(OH)(CH_3)_2$ | trans | oil | c,e |
| 26 | " | H | H | $CH_3$ | H | $-C{=}C-C(OH)(C_2H_5)_2$ | trans | oil | b,c,e |
| 27 | " | H | H | $CH_3$ | H | $-C{\equiv}C-CH(OH)-(CH_2)_3-CH_3$ | trans | oil | b,c,e |
| 28 | " | H | H | $CH_3$ | H | $-C{\equiv}C-C(OH)(CH_3)(C_2H_5)$ | trans | oil | b,c,e |
| 29 | " | H | H | $CH_3$ | H | $-C{=}C-C(OH)(CH_3)(C(CH_3)_3)$ | trans | oil | b,c,e |
| 30 | " | H | H | $CH_3$ | H | $-C{\equiv}C-(CH_2)_3-CH_3$ | trans | mp (hydrochloride) 118–121° | a, e |
| 31 | " | H | H | $CH_3$ | H | $-C{\equiv}C-(CH_2)_2-CH_3$ | trans | oil | a,c,e |
| 32 | " | H | H | $CH_3$ | H | $-C{\equiv}C-(CH_2)_4-CH_3$ | trans | oil | a,c,e |
| 33 | " | H | H | $CH_3$ | H | $-C{\equiv}C-(CH_2)_5-CH_3$ | trans | oil | a,c,e |
| 34 | " | H | $R_3 + R_4 + N$ (piperidine ring) | | H | $-C{\equiv}C-(CH_2)_2-CH_3$ | trans | oil | a,c |
| 35 | " | H | " | | H | $-C{\equiv}C-(CH_2)_3-CH_3$ | trans | oil | a,c |
| 36 | " | H | H | $CH_3$ | H | $-C{\equiv}C-CH{=}CH-(CH_2)_2-CH_3$ | trans | oil | a,c,e |
| 37 | " | H | H | $CH_3$ | H | $-C{\equiv}C-C(C_2H_5){=}CH\cdot CH_3$ | trans | oil | a,c,d e |

TABLE I-continued

| Example | R₁ | R₂ | R₃ | R₄ | R₅ | R₆ | Conf. | Physical data | Proc. |
|---|---|---|---|---|---|---|---|---|---|
| 38 | " | H | H | CH₃ | H | −C≡C−C(CH₃)=CH.CH₃ | trans | oil | a,c,d,e |
| 39 | " | H | H | CH₃ | H | −C≡C−C(C(CH₃)₃)=CH₂ | trans | oil | a,c,d,e |
| 40 | " | H | H | CH₃ | H | −C(C₆H₅)=CH₂ | trans | oil | c,d,e |
| 41 | " | H | H | CH₃ | H | −C(CH₂.CH(CH₃)CH₃)=CH₂ | trans | oil | c,d,e |
| 42 | " | H | H | CH₃ | H | −C((CH₂)₃−CH₃)=CH₂ | trans | oil | c,d,e |
| 43 | " | H | H | CH₃ | H | −C(C(CH₃)₃)=CH₂ | trans | oil | c,d,e |
| 44 | " | H | H | CH₃ | H | −C(CH₃)=CH−C₆H₄−H  and  −C(=CH₂)−CH₂−C₆H₄−H | trans | oil | c,e |
| 45 | " | H | H | CH₃ | H | −CH=CH−C₆H₄−H | trans | oil | c,d |
| 46 | " | H | H | CH₃ | H | −C≡C−CH₂OH | trans | oil | b,c,e |
| 47 | " | H | H | CH₃ | CH₃ | −C≡C−(CH₂)₃−CH₃ | trans | oil | a,c,e |
| 48 | " | H | H | CH₃ | CH₃ | " | cis | oil | a,e |
| 49 | " | H | H | CH₃ | H | −C≡C−C(CH₃)(CH₃)−C₂H₅ | trans | oil | a,c,e |
| 50 | " | H | H | CH₃ | H | " | cis | oil | a,e |
| 51 | " | H | H | CH₃ | H | −C≡C−(cyclopentyl-H) | trans | oil | a,c,e |
| 52 | " | H | H | CH₃ | H | " | cis | oil | a,c |
| 53 | " | H | H | CH₃ | H | −C≡C−(norbornyl) | trans | oil | a,c,e |
| 54 | " | H | H | CH₃ | H | " | cis | oil | a,e |
| 55 | benzothiophene | H | H | CH₃ | H | −CH=CH−C₆H₄−H | trans | oil | c,d,e |

TABLE I-continued

| Example | R₁ | R₂ | R₃ | R₄ | R₅ | R₆ | Conf. | Physical data | Proc. |
|---|---|---|---|---|---|---|---|---|---|
| 56 | 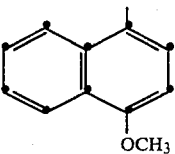 | H | H | $CH_3$ | H | $-C{\equiv}C-C(CH_3)_3$ | cis | oil | a,c,e |
| 57 | " | H | H | $CH_3$ | H | " | cis | oil | a,e |
| 58 | $R_1 + R_2$ 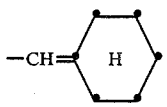 | | H | $CH_3$ | H | $-CH{=}\langle\text{phenyl}\rangle$ | trans | oil | c,d,e |
| 59 | " | | H | $CH_3$ | H | $-C{\equiv}C-C(CH_3)_3$ | trans | oil | a,c,e |

In the following table NMR data are given. Data comprises peaks in ppm relative to TMS as standard in $CDCL_3$. Types of peaks are
m = multiplet
dt = double triplet
dm = double multiplet
s = singlet
d = doublet
t = triplet
ps.t = pseudo triplet
dd = double doublet
dbr = double broad
br = broad
qua = quartet
mbr = multiple broad
sext = sextuplet
ddd = double double doublet
sbr = single broad

| Example | Isomer | Spectrum |
|---|---|---|
| 1,7 | trans | δ = 7.7–8.0 (m, 2H); 7.15–7.45 (m, 4H); 6.14 (dt, J=16 and 2 × 6.5 Hz, 1 olef. H); 6.65 (dm, J=16 Hz, 1 olef. H); 3.72 (s, 2H); 3.10 (d, J=6.5 Hz, 2H); 2.3 (m, 2H); 2.24 (s, 3H); 1.2–1.7 (m, 4H); 0.9 (ps.t., 3H). |
| 1,8 | cis | δ = 7.7–8.0 (m, 2H); 7.15–7.45 (m, 4H); 6.0 (dt, J=11 and 2 × 6.5 Hz, 1 olef. H); 5.64 (dm, J=11 Hz, 1 olef. H); 3.66 (s, 2H); 3.35 (d, J=6.5 Hz, 2H); 2.34 (m, 2H); 2.28 (s, 3H); 1.2–1.7 (m, 4H); 0.9 (ps.t., 3H). |
| 9 | cis | δ = 8.2–8.4 (m, 1H); 7.7–7.9 (m, 2H); 7.3–7.6 (m, 4H); 6.05 (dt, J=10.8 + 2 × 7 Hz, 1 olef. H); 5.65 (dm, J=10.8 Hz, 1 olef. H); 3.92 (s, 2H); 3.38 (dd, J=7 u. 1.5 Hz, 2H); 2.34 (m, 2H); 2.25 (s, 3H); 1.2–1.8 (m, 4H); 0.94 (m, 3H). |
| 10 | trans | δ = 6.9–7.2 (m, 3H); 6.12 (dt, J=16 and 2 × 6.5 Hz, 1 olef. H); 5.64 (dm, J=16 Hz, 1 olef. H); 3.4 (s, 2H); 3.05 (d, J=6.5 Hz, 2H); 2.7–2.9 (m, 4H); 2.2–2.4 (m, 2H); 2.18 (s, 3H); 1.65–1.9 (m, 4H); 1.3–1.7 (m, 4H); 0.92 (m, 3H). |
| 11 | cis | δ = 6.85–7.2 (m, 3H); 5.97 (dt, J=11 and 6.5 Hz, 1 olef. H); 5.60 (dm, J=11 Hz, 1 olef. H); 3.45 (s, 2H); 3.30 (d, J=6.5 Hz, 2H); 2.7–2.9 (m, 4H); 2.2–2.4 (m, 2H); 2.22 (s, 3H); 1.7–1.9 (m, 4H); 1.3–1.7 (m, 4H); 0.95 (m, 3H). |
| 12 | trans | δ = 7.1–7.8 (m, 5H); 6.14 (dt, J=16 and 2 × 6.5 Hz, 1 olef. H); 5.65 (dm, J=16 Hz, 1 olef. H); 3.63 (s, 2H); 3.1 (d, J=6.5 Hz, 2H); 2.2–2.4 (m, 2H); 2.25 (s, 3H); 1.2–1.7 (m, 4H); 0.9 (m, 3H). |
| 13 | cis | δ = 7.1–7.8 (m, 5H); 6.0 (dt, J=11 and 2 × 6.5 Hz, 1 olef. H); 5.64 (dm, J=11 Hz, 1 olef. H); 3.66 (s, 2H); 3.35 (d, J=6.5 Hz, 2H); 2.2–2.4 (m, 2H); 2.30 (s, 3H); 1.2–1.7 (m, 4H); 0.9 (m, 3H). |
| 16 | trans | δ = 8.2–8.35 (m, 1H); 7.7–7.9 (m, 2H); 7.3–7.6 (m, 4H); 6.18 (dt, J=17 and 2×7 Hz); 5.65 (dm, J=17 Hz, 1H); 3.9 (s, 2H); 3.12 (dd, J=7 u. 1 Hz, 2H); 2.22 (s, 3H); 1.25 (s, 9H). |
| 17 | cis | δ = 8.2–8.35 (m, 1H); 7.7–7.9 (m, 2H); 7.3–7.6 (m, 4H); 6.03 (dt, J=11 and 2 × 6.5 Hz, 1H); 5.65 (dbr, J=11 Hz, 1H); 3.92 (s, 2H); 3.38 (d, J=6.5 Hz, 2H); 2.26 (s, 3H); 1.27 (s, 9H). |
| 18 | trans | δ = 8.2–8.35 (m, 1H); 7.7–7.9 (m, 2H); 7.2–7.6 (m, 9H); 6.36 (dt, J=16 and 2 × 6.5 Hz, 1H); 5.9 (dm, J=16 Hz, 1H); 3.94 (s, 2H); 3.22 (d, J=6.5 Hz, 2H); 2.28 (s, 3H). |
| 19 | cis | δ = 8.2–8.4 (m, 1H); 7.7–7.9 (m, 2H); 7.2–7.6 (m, 9H); 6.20 (dt, J=11 and 2 × 6.5 Hz, 1H); 5.85 (d, J=11 Hz, 1H); 3.98 (s, 2H); 3.50 (d, J=6.5 Hz, 2H); 2.30 (s, 3H). |
| 20 | trans | δ = 8.2–8.4 (m, 1H); 7.7–7.9 (m, 2H); 7.3–7.6 (m, 4H); 6.20 (dt, J=16 and 2 × 6.5 Hz, 1H); 5.80 (dm, J=16 Hz, 1H); 3.90 (s, 2H); 3.14 (d, J=6.5 Hz, 2H); 2.5 (m, 1H); 2.24 (s, 3H); 1.2–1.7 (m, 2H); 1.18 (d, J=7 Hz, 3H); 1.0 (t, J=7 Hz, 3H). |
| 21 | cis | δ = 8.2–8.4 (m, 1H); 7.7–7.9 (m, 2H); 7.3–7.6 (m, 4H); 6.05 (dt, J=11 and 2 × 6.5 Hz, 1H); 5.67 (dm, J=11 Hz, 1H); 3.94 (s, 2H); 3.40 (d, J=6.5 Hz, 2H); 2.55 (m, 1H); 2.28 (s, 3H); 1.2–1.8 (m, 2H); 1.20 (d, J=7 Hz, 3H); 1.02 (t, J=7 Hz, 3H). |
| 22 | trans | δ = 8.2–8.35 (m, 1H); 7.65–7.9 (m, 2H); 7.3–7.6 (m, 4H); 6.20 (dt, J=16 and 2 × 6.5 Hz, 1H); 5.68 (dm, J=16 Hz, 1H); 3.88 (s, 2H); 3.13 (d, J=6.5 Hz, 2H); 2.22 (s, 3H); 2.2 (m, 2H); 1.6–2.1 (m, 1H); 1.0 (d, J=7 Hz, 6H). |
| 23 | cis | δ = 8.2–8.4 (m, 1H); 7.7–7.9 (m, 2H); 7.3–7.6 (m, 4H); 6.04 (dt, J=12 and 2 × 7 Hz, 1H); 5.65 (dbr, J=12 Hz, 1H); 3.90 (s, 2H); 3.38 (d, J=7 Hz, 2H); 2.24 (s, 3H); 2.2 (m, 2H); 1.6–2.0 (m, 1H); 1.0 (d, J=7 Hz, 6H). |

-continued

| Example | Isomer | Spectrum |
|---|---|---|
| 24 | trans | δ = 8.2–8.4 (m, 1H); 7.65–7.9 (m, 2H); 7.3–7.6 (m, 4H); 7.15–7.3 (m, 2H); 6.95 (m, 1H); 6.36 (dt, J=16 u. 2 × 6 Hz, 1H); 5.9 (dbr, J=16 Hz, 1H); 3.92 (s, 2H); 3.20 (d, J=6 Hz, 2H); 2.28 (s, 3H). |
| 3,30 | trans | δ = 8.2–8.35 (1 arom. H); 7.7–7.9 (2 arom. H); 7.3–7.6 (4 arom. H); 6.17 (dt, 1 olef. H, J=16 + 2 × 6.5 Hz); 5.67 (d, 1 olef. H, J=16 Hz); 3.89 (s, 2H); 3.13 (d, 2H, J=6.5Hz); 2.21 (s, 3H); 2.2–2.4 (m, 2H); 1.2–1.8 (4H); 0.8–1.05 (m, 3H). |
| 31 | trans | identical with Ex. 3,30 except: δ = 2.28 (t, 2H); 1.55 (sext., 2H); 1.0 (t, 3H). |
| 32 | trans | identical with Ex. 3,30 except: δ = 1.2–1.8 (m, 6H). |
| 33 | trans | identical with Ex. 3,30 except: δ = 1.2–1.8 (m, 8H). |
| 34 | trans | δ = 8.5 (br, 1H); 7.3–7.9 (m, 6H); 6.02 (ddd, J=5, 8 + 16 Hz, 1H); 5.46 (dbr. J=16 Hz, 1H); 3.80 (br, 1H); 3.1–3.35 (m, 2H); 2.52 (dd, 8 + 14 Hz, 1H); 2.0–2.35 (m, 3H); 1.6–2.0 (m, 6H); 1.54 (sext., J=7 Hz, 2H); 0.97 (t, J=7 Hz, 3H). |
| 35 | trans | identical with Ex. 34 except: δ = 1.3–1.7 (m, 4H); 0.9 (ps.t, 3H). |
| 4,36 | trans | δ = 8.2–8.35 (m, 1H); 7.7–7.9 (m, 2H); 7.3–7.6 (m, 4H); 6.26 (dt, J=15.5 + 2× 6.5 Hz, 1H); 5.9 (dt, J=11 + 2×7 Hz); 5.85 (d, J=15.5 Hz, 1H); 5.58 (dbr, J= 11 Hz, 1H); 3.92 (s, 2H); 3.18 (d, J=6.5 Hz, 2H); 2.35 (t, 2H); 2.26 (s, 3H); 1.2–1.7 (m, 2H); 0.95 (ps.t. 3H). |
| 37 | trans | δ = 8.15–8.35 (m, 1H); 7.7–7.9 (m, 2H); 7.3–7.6 (m, 4H); 6.25 (dt, J=16 + 6 Hz, 1H); 5.86 (d, J=16 Hz, 1H); 5.70 (t, J = 7 Hz, 1H); 3.94 (s, 2H); 3.20 (d, J=6 Hz, 2H); 2.26 (s, 3H); 2.16 (qua, J=8 Hz, 2H); [1.8 (d, J=7 Hz) und 1.7 (d, J=7 Hz) Σ 3H, in ratio 6/1]; 1.06 (t, 3H). |
| 38 | trans | δ = 8.2–8.35 (m, 1H); 7.7–7.9 (m, 2H); 7.3–7.6 (m, 4H); 6.30 (dt, J=16 + 2×6 Hz, 1H); 5.86 (d,J=16 Hz, 1H); 5.75 (m, 1H); 3.92 (s, 2H); 3.18 (d, J=6 Hz, 2H); 2.26 (s, 3H); 1.87 (s, 3H); 1.8 u. 1.7 (2 d, 3H). |
| 39 | trans | δ = 8.2–8.4 (m, 1H); 7.7–7.9 (m, 2H); 7.3–7.6 (m, 4H); 6.28 (dt, J=16 + 2×6.5 Hz, 1H); 5.84 (dm, J=16 Hz, 1H); 5.30 (m, =C(H/H) ); 3.92 (s, 2H); 3.18 (d, J=6.5 Hz, 2H); 2.26 (s, 3H); 1.18 (s, 9H). |
| 5,44 A | trans | δ = 8.2–8.35 (1 arom. H); 7.7–7.9 (2 arom. H); 7.3–7.6 (4 arom. H); 6.22 (d, 1 olef. H, J=16 Hz); 5.93 (dt, 1 olef. H, J=16 + 2 × 6.5 Hz); 4.87 u. 4.83 (=C(H/H)); 3.90 (s, 2H); 3.19 (d, 2H, J=6.5 Hz); 2.25 (s, 3H); 1.0–2.4 (11 H, Cyclohexyl). |
| B | trans | δ = 8.2–8.35 (1 arom. H); 7.7–7.9 (2 arom. H); 7.3–7.6 (4 arom. H); 6.79 (d, 1 olef. H, J=16 Hz); 5.80 (dt, 1 olef. H, J=16 + 2 × 6.5 Hz); 3.92 (s, 2H); 3.24 (d, 2H, J=6.5 Hz); 2.2–2.5 (m, 4H); 2.26 (s, 3H); 1.88 (s, 3H); 1.58 (br, 6H). |
| 40 | trans | δ = 8.15–8.30 (m, 1H); 7.7–7.9 (m, 2H); 7.3–7.6 (m, 9H); 6.51 (d, J=18 Hz, 1H); 5.82 (dt, J=18 + 2 × 7.5 Hz, 1H); [5.26 (sbr, 1H) + 5.14 (d, J=2 Hz, 1H) =C(H/H) ]; 3.88 (s, 2H); 3.20 (d, J=7.5 Hz, 2H); 2.22 (s, 3H). |
| 41 | trans | δ = 8.2–8.35 (m, 1H); 7.7–7.9 (m, 2H); 7.3–7.6 (m, 4H); 6.24 (d, J = 16 Hz, 1 olef. H); 5.85 (dt, J=16 + 2 × 6.5 Hz, 1 olef. H); 4.95 (dd, J=11 + 2 Hz, 2 olef. H); 3.9 (s, 2H); 3.18 (d, J=6.5 Hz, 2H); 2.24 (s, 2H); 2.13 (d, J=6.5 Hz, 2H); 1.6–2.1 (m, 1H); 0.9 (d, J=6.5 Hz, 6H). |
| 42 | trans | δ = 8.2–8.35 (m, 1H); 7.65–7.9 (m, 2H); 7.3–7.6 (m, 4H); 6.26 (d, J=16 Hz, 1H); 5.86 (dt, J=16 + 2 × 6.5 Hz, 1H); 4.95 (s, =C(H/H) ); 3.90 (s, 2H); 3.18 (d, J=6.5 Hz, 2H); 2.24 (s, 3H); 2.15–2.35 (m, 2H); 1.1–1.7 (m, 4H); 0.9 (ps.t, 3H). |
| 43 | trans | δ = 8.2–8.35 (m, 1H); 7.7–7.9 (m, 2H); 7.3–7.6 (m, 4H); 6.30 (d, J=15.5 Hz, 1H); 6.02 (dt, J=15.5 Hz + 2 × 6.5 Hz, 1H); [5.07 (sbr, 1H) + 4.80 (d, J=2 Hz, 1H), =C(H/H) ]; 3.9 (s, 2H); 3.16 (d, 2H); 2.25 (s, 3H); 1.1 (s, 9H). |
| 6,45 | trans | δ = 8.2–8.35 (1 arom. H); 7.7–7.9 (2 arom. H); 7.3–7.6 (4 arom. H); 6.52 (dd, 1 olef. H, J=15 u. 10 Hz); 5.86 (d, 1 olef. H, J=10 Hz); 5.79 (dt, 1 olef. H, J=15 + 2 × 6.5 Hz); 3.92 (s, 2H); 3.20 (d, J= 6.5 Hz, 2H); 2.25 (s, 3H); 2.1–2.4 (m, 4H); 1.6 (br, 6H). |
| 46 | trans | δ = 8.15–8.35 (m, 1H); 7.7–7.9 (m, 2H); 7.3–7.6 (m, 4H); 6.3 (dt, J=16 + 2×6.5 Hz, 1H); 5.7 (dm, J=16 Hz, 1H); 4.34 (d, J=2 Hz, 2H); 3.9 (s, 2H); 3.16 (d, J=6.5 Hz, 2H); 2.24 (s, 3H); 2.2 (OH). |
| 47 | trans | δ = 8.2–8.35 (m, 1H); 7.65–7.9 (m, 2H); 7.3–7.5 (m, 4H); 6.17 (dd, J=16 + 7 Hz, 1H); 5.58 (dm, J=16 Hz, 1H); 3.9 (AB-System, 2H); 3.25 (m, 1H); 2.1–2.3 (m, 2H); 2.14 (s, 3H); 1.3–1.6 (m, 4H); 1.18 (d, J=7 Hz, 3H); 0.85 (m, 3H). |
| 48 | cis | δ = 8.2–8.35 (m, 1H); 7.6–7.9 (m, 2H); 7.3–7.6 (m, 4H); 5.98 (dd, J=11 + 9 Hz, 1H); 5.6 (dm, J=11 Hz, 1H); 3.96 (AB-System, 2H); 3.8 (m, 1H); 2.1–2.3 (m, 2H); 2.16 (s, 3H); 1.2–1.6 (m, 4H); 1.26 (d, J=7 Hz, 3H); 0,82 (m, 3H). |
| 49 | trans | δ = 8.15–8.35 (m, 1H); 7.6–7.9 (m, 2H); 7.3–7.6 (m, 4H); 6.14 (dt, J=16 + 2×6.5 Hz, 1H); 5.66 (dm, J=16 Hz, 1H); 3.86 (s, 2H); 3.10 (d, J=6.5 Hz, 2H); 2.2 (s, 3H); 1.4 (qua, J=7 Hz, 2H); 1.15 (s, 6H); 0.9 (t,J=7 Hz, 3H). |
| 50 | cis | δ = 8.2–8.35 (m, 1H); 7.6–7.9 (m, 2H); 7.3–7.6 (m, 4H); 6.0 (dt, J=11 + 2×6.5 Hz, 1H); 5.64 (dm, J=11 Hz, 1H); 3.9 (s, 2H); 3.35 (d, J=6.5 Hz, 2H); 2.22 (s, 3H); 1.45 (qua, J=7 Hz, 2H); 1.18 (s, 6H); 0.95 (t, J=7 Hz, 3H). |
| 51 | trans | δ = 8.15–8.35 (m, 1H); 7.6–7.9 (m, 2H); 7.3–7.6 (m, 4H); 6.16 (dt, J=16 + 2×6.5 Hz, 1H); 5.66 (dm, J=16 Hz, 1H); 3.86 (s, 2H); 3.10 (d, J=6.5 Hz, 2H); 2.7 (br, 1H); 2.2 (s, 3H); 1.4–2.1 (m, 8H). |
| 52 | cis | δ = 8.15–8.35 (m, 1H); 7.6–7.9 (m, 2H); 7.3–7.6 (m, 4H); 6.0 (dt, J=11 + 2×6.5 Hz, 1H); 5.64 (dm, J=11 Hz, 1H); 3.9 (s, 2H); 3.36 (d, J=6.5 Hz, 2H); 2.75 (br, 1H); 2.22 (s, 3H); 1.4–2.1 (m, 8H). |
| 55 | trans | δ = 7.8–8.1 (m, 2H); 7.25–7.5 (m, 3H); 6.50 (dd, J=17 + 12 Hz, 1H); 5.85 (d, J=12 Hz, 1H); 5.74 (dt, J=17 u. 2×7 Hz, 1H); 3.77 (s, 2H); 3.14 (d, J=7 Hz, 2H); 2.0–2.4 (m, 4H); 2.25 (s, 3H); 1.55 (sbr, 6H). |
| 56 | trans | δ = 8.2–8.4 (m, 2H); 7.25–7.7 (m, 3H); 6.74 (d, J=8 Hz, 1H); 6.2 (dt, J=18 + 2×7 Hz, 1H); 5.67 (dt, J=18 u. 2×15 Hz, 1H); 4.0 (s, 3H); 3.82 (s, 2H); 3.10 (dd, J=7 u. 1.5 Hz, 2); 2.2 (s, 3H); 1.24 (s, 9H). |
| 57 | cis | δ = 8.2–8.4 (m, 2H); 7.25–7.7 (m, 3H); 6.74 (d, J=8 Hz, 1H); 6.05 (dt, J=12 + 2×7.5 Hz, 1H); 5.65 (dt, J=12 u. 2×1.5 Hz, 1H); 4.0 (s, 3H); 3.85 (s, 2H) 3.35 (dd, J=7.5 u. 1.5 Hz, 2H); |

-continued

| Example | Isomer | Spectrum |
| --- | --- | --- |
| 58 | trans | 2.24 (s, 3H); 1.26 (s, 9H).<br>δ = 7.2–7.8 (m, 6H); 6.44 (dd, J=17 + 12 Hz, 1H); 5.80 (d, J=12 Hz, 1H); 5.66 (dt, J=17 + 2×7 Hz, 1H); 5.0 (t, J=6 Hz, 1H); 3.33 (d, J=6 Hz, 2H); 3.14 (d, J=7 Hz, 2H); 2.0–2.4 (m, 4H); 2.12 (s, 3H); 1.5 (sbr, 6H). |
| 59 | trans | δ = 7.1–7.7 (m,6H); 6.04 (dt,J=16 + 2×6.5 Hz, 1H); 5.6 (dm,J=16 Hz, 1H); 4.9 (t,J=6 Hz, 1H); 3.22 (d,J=6 Hz, 2H); 3.0 (d,J=6.5 Hz, 2H); 2.1 (s, 3H); 1.18 (s, 9H). |
| 53 | trans | δ = 8.15–8.35 (m, 1H); 7.6–7.9 (m, 2H); 7.3–7.6 (m, 4H); 6,15 (dt,J=16 + 2×6.5 Hz, 1H); 5.65 (dm, J=16 Hz, 1H); 3.85 (s, 2H); 3.10 (d, J=6.5 Hz, 2H); 2.2 (s, 3H); 1.8–2.1 (br, 9H); 1.6–1.8 (br, 6H). |

The required starting materials can be obtained e.g. as follows.

1. Compounds of formula IV (A) (3-Benzo[b]thiophenemethyl)methylamine (for Ex. 1)

3-Chloromethylbenzo[b]thiophene is dissolved in benzene, added dropwise to a ca. 10-fold excess of methylamine in ethanol at 0°–5° and then stirred for 16 hours at room temperature. The crude mixture is concentrated under vacuum, the residue partitioned between methylenechloride and 1N NaOH and the organic phase dried and evaporated under vacuum. The purified product is obtained by vacuum distillation b.p. 90°–94°/1,33 Pa.

(B) (3-Benzo[b]furanmethyl)methylamine (for Ex. 12 and 13)

Obtained analogously to Example A) b.p. 105°–110°/5.3 Pa.

(C) 2-(1-Naphthyl)piperidine (for Ex. 15, 34 and 35)

A Grignard complex is prepared by adding 43.4 g of 1-bromonaphthalene in absolute ether dropwise to 5.1 g of magnesium in 50 ml of absolute ether. The ether is removed from the reaction mixture and replaced by absolute benzene. 8 g 6-Methoxy-2,3,4,5-tetrahydropyridine are added to the boiling reaction mixture. Afte a further 8 hours the mixture is cooled, treated with saturated aqueous ammoniumchloride solution and the reaction product removed from the organic phase by shaking with aqueous HCl-solution. After neutralisation and working up the 2-(1-naphthyl)-3,4,5,6-tetrahydropyridine is dissolved directly in methanol and reduced with NaBH$_4$. After normal working up the product is converted with alcoholic HCl solution to its hydrochloride. M.p. 287°–289° (after intensive drying under high vacuum 328°–329°).

2. Compounds of formula V (D) 1-Bromo-6,6-dimethyl-2-hepten-4-yne (for Ex. 16, 17, 56, 57 and 59)

(a) 6,6-Dimethyl-1-hepten-4-yn-3-ole:

38 ml 3,3-Dimethyl-1-butyne are dissolved in abs. tetrahydrofuran and 172 ml of a 20% solution of n-butyl-lithium added dropwise under protective gas at a temperature of −20°. The reaction mixture is then cooled to −75° and 19.3 g acrolein in 20 ml of tetrahydrofuran added dropwise. The mixture is warmed to room temperature, reacted with saturated aqueous NH$_4$Cl and extracted a number of times with ether. The organic phase is dried, concentrated and the purified product obtained by vacuum distillation, b.p. 70°–72°/1600 Pa.

(b) 1-Bromo-6,6-dimethyl-2-hepten-4-yne:

50 ml 48% HBr and 10 g PBr$_3$ are stirred at 40° until a homogenous mixture is obtained. An alcoholic solution of 13.5 g 6,6-dimethyl-1-hepten-4-yn-3-ole are added dropwise at 10° and stirred for 1½ hours at room temperature. The reaction mixture is poured onto ice and extracted a number of times with hexane. The organic phase is washed a number of times with aqueous NaCl, dried and concentrated. NMR-spectrography shows that the oily product comprises a 3:1 mixture of trans- and cis-1-bromo-6,6-dimethyl-2-hepten-4-yne and is taken directly for alkylation.

NMR: δ=5.5–6.4 (m, 2 olef. H), [4.15 (d. J=8 Hz) and 3.95 (d, J=8 Hz) in ratio 1:3, 2H, =CH—CH$_2$Br], 1.20 (m, 9H).

Analogously to (D) above the following compounds of formula V can be obtained.

TABLE II $$a \quad R_5-CH=CH-\overset{OH}{\underset{|}{CH}}-C\equiv C-R_{11}$$

$$b \quad A-CH-CH=CH-C\equiv C-R_{11}$$
$$\phantom{b \quad A-}\underset{R_5}{|}$$

| | R$_{11}$ | R$_5$ | A | Physical data | for Ex. |
| --- | --- | --- | --- | --- | --- |
| (E) a<br>b | —CH(CH$_3$)(C$_2$H$_5$) | H | —<br>Br | b.p. 75–80°/1460 Pa<br>oil | 20,21 |
| (F) a<br>b | —CH$_2$.CH(CH$_3$)$_2$ | H | —<br>Br | b.p. 87–91°/1730 Pa<br>oil | 22,23 |
| (G) a<br>b | —C(CH$_3$)$_2$C$_2$H$_5$ | H | —<br>Br | b.p. 90°/1460 Pa<br>oil | 49,50 |
| (H) a<br>b | cyclopentyl | H | —<br>Br | b.p. 94–96°/800 Pa<br>oil | 51,52 |
| (I) a<br>b | —(CH$_2$)$_3$—CH$_3$ | CH$_3$ | —<br>Br | b.p. 92–93°/530 Pa<br>oil | 47,48 |

The remaining compounds of formula V can be obtained analogously to (D) above.

3. Compounds of formula VIII (M) N-Methyl-N-(1-naphthylmethyl)octa-2,4-diynyl-1-amine (for Ex. 31)

9 g 1,3-Heptadiyne, 16 g methyl-(1-naphthylmethyl)amine, 2.8 g paraformaldehyde and 1.3 g ZnCl$_2$ (anhydrous) are heated for 3 hours at 100° in absolute dioxane. After cooling the solvent is removed under vacuum, the residue partitioned between chloroform and aqueous NaHCO$_3$-solution and the organic phase dried and concentrated. The purified product is obtained by chromatography over kieselgel (toluene/ethyl acetate 9:1) as an oil.

(N) N-Methyl-N-(1-naphthylmethyl)-2,4-nonadiynyl-1-amine (for Ex. 3)

8.25 g 1-Bromohexyne are added dropwise to a mixture of 16 g N-methyl-N-(1-naphthylmethyl)-propargylamine, 0.5 g NH$_2$OH.HCl, 0.25 g CuCl and 20 ml 70% ethylamine. The reaction mixture is stirred overnight at room temperature, treated with an aqueous solution of 1 g KCN and extracted a number of times with ether. The organic phase is washed with saturated aqueous NaCl, dried and evaporated. The title substance is obtained as an oil after chromatography over Kieselgel (eluant toluene/ethyl acetate 95:5).

(O) N-Methyl-N-(1-naphthylmethyl)-4-t.butyl-pent-2-yn-4-enyl-1-amine (for Ex. 43)

933 mg N-Methyl-N-(1-naphthylmethyl)-4-hydroxy-4,5,5-trimethyl-2-hexynyl-1-amine are dissolved in abs. pyridine, warmed to 50° and 0.4 ml POCl$_3$ added. Stirring is carried out for one hour at 90°, the mixture poured onto ice and the reaction product isolated as an oil by extraction with ether and chromatography over kieselgel (eluant toluene/ethyl acetate 9:1).

Analogously to (M), (N) and (O) above, the following compounds of formula VIII may be obtained.

TABLE III

Structure: naphthyl-CH—N(R$_3$)(R$_4$)—C≡C—R$_6$

| | R$_3$ | R$_4$ | R$_6$ | Physical data | For Ex. |
|---|---|---|---|---|---|
| (P) | H | CH$_3$ | —C≡C—(CH$_2$)$_4$—CH$_3$ | oil | 32 |
| (Q) | H | CH$_3$ | —C≡C—(CH$_2$)$_5$—CH$_3$ | oil | 33 |
| (R) | H | CH$_3$ | —C≡C—C(CH$_3$)$_3$ | oil | 16 |
| (S) | R$_3$ + R$_4$ + N | | —C≡C—(CH$_2$)$_2$—CH$_3$ | oil | 34 |
| (T) | piperidinyl (N-) | | —C≡C—(CH$_2$)$_3$—CH$_3$ | oil | 35 |

The remaining compounds of formula VIII can be prepared analogously to (M), (N) and (O) above.

4. Compounds of formula If (U) N-Methyl-N-(1-naphthylmethyl)-4-hydroxy-4-cyclohexyl-2-pentenyl-1-amine (for Ex. 5)

(a) N-Methyl-N-(1-naphthylmethyl)-4-hydroxy-4-cyclohexylpent-2-ynyl-1-amine:

10.7 ml of a 15% solution of BuLi in hexane are added dropwise to 3 g N-methyl-N-(1-naphthylmethyl)propargyl amine in absolute tetrahydrofuran and after 30 minutes reacted with a solution of 1.79 g cyclohexylmethyl ketone. Stirring is continued for 24 hours at room temperature and the mixture poured onto ice and extracted with ether. The organic phase is washed, dried and concentrated under vacuum. Chromatography over kieselgel (eluant toluene/ethylacetate 4:1) yields the title product as an oil.

(b) N-Methyl-N-(1-naphthylmethyl)-4-hydroxy-4-cyclohexyl-2-pentenyl-1-amine:

10 g of the substance obtained under (a) are dissolved in tetrahydrofuran and added dropwise to a suspension of 1.4 g LiAlH$_4$ in abs. tetrahydrofuran and the mixture refluxed for 3 hours. Excess reagent is destroyed with ethyl acetate/H$_2$O. After extraction with ether, drying and evaporation under vacuum followed by chromatography over kieselgel (eluant CHCl$_3$/C$_2$H$_5$OH 95:5) the title product is obtained as an oil.

Analogously to (U) above the following compounds can be obtained.

TABLE IV (a) naphthyl-CH$_2$—N(CH$_3$)—CH$_2$—C≡C—C(CH$_3$)(OH)—R$_x$ (b) naphthyl-CH$_2$—N(CH$_3$)—CH$_2$—CH=CH—C(CH$_3$)(OH)—R$_x$

| | R$_x$ | physical data [(a) and (b)] | For Ex. |
|---|---|---|---|
| (V) (a) (b) | —CH$_2$—CH(CH$_3$)$_2$ | oil | 41 |
| (W) (a) (b) | —(CH$_2$)$_3$—CH$_3$ | oil | 42 |
| (X) (a) (b) | —C(CH$_3$)$_3$ | oil | 43 |
| (Y) (a) (b) | —C$_6$H$_5$ | oil | 40 |

Compounds of formula IX can be prepared analogously to Example 6 above and are preferably taken directly without further purification or isolation for the final step.

| Example | Spectrum |
|---|---|
| (N) | δ = 8.2–8.35 (1 arom. H); 7.7–7.9 (2 arom. H); 7.3–7.6 (4 arom. H); 3.97 (s, 2H); 3.37 (s, 2H) 2.40 (s, 3H); 2.2.–2.4 (m, 2H); 1.2–1.8 (4H); 0.8–1.05 (m, 3H). |
| (M) | identical with (N) except: δ = 2.28 (t, 2H); 1.58 (sext., 2H); 1.0 (t, 3H) |
| (P) | identical with (N) except: δ = 1.2–1.8 (m, 6H). |
| (Q) | identical with (N) except: δ = 1.2–1.8 (m, 8H). |
| (R) | δ = 8.1–8.25 (m, 1H); 7.6–7.85 (m, 2H); 7.2–7.5 (m, 4H); 3.92 (s, 2H); 3.33 (s, 2H) 2.35 (s,3H); 1.22 (s, 9H). |
| (S) | δ = 8.5 (br, 1H), 7.3–7.9 (m, 6H), 4.05 (br, 1H); 3.24 (s, 2H); 3.12 (m, 1H); 2.5–2.8 (m, 1H), 2.26 (t, J=6.5 Hz, 2H); 1.6–2.0 (m, 6H), 1.56 (sext., J=7 Hz, 2H); 0.99 (t, J=7 Hz, 3H). |
| (T) | identical with (S) except: δ = 2.28 (ps.t, 2H); 1.3–1.7 (m, 4H); 0.91 (ps.t, 3H). |
| (U) | (a) δ = 8.2–8.35 (1 arom. H); 7.7–7.9 (2 arom. H); 7.3–7.6 (4 arom. H); 4.0 (s, 2H); 3.37 (s, 2H); |

| Example | Spectrum |
|---|---|
| | 2.38 (s, 3H); 1.52 (s, 3H); 1.0-2.2 (11H). |
| (b) | δ = 8.2-8.35 (1 arom. H); 7.7-7.9 (2 arom.H); 7.3-7.6 (4 arom. H); 5.76 (m, 2 olef. H); 3.91 (s, 2H); 3.13 (m, 2H); 2.25 (s, 3H); 1.23 (s, 3H); 0.8-2.0 (11H). |
| (V) (a) | δ = 8.15-8.35 (m, 1H); 7.7-7.9 (m, 2H); 7.3-7.6 (m, 4H); 3.95 (s, 2H); 3,34 (s, 2H); 2.35 (s, 3H); 1.8-2.3 (m, 1H); 2.0 (s, O$\underline{H}$); 1.62 (d, J=6.5 Hz, 2H); 1.53 (s, 3H); 1.04 u. 1.02 (2 d, J=6.5 Hz, Σ 6H). |
| (b) | δ = 8.2-8.4 (m, 1H); 7.7-7.9 (m, 2H); 7.3-7.6 (m, 4H); 5.78 (AB-portion of an $ABX_2$-system, 2 olef. H); 3.90 (s, 2H); 3.12 (m, 2H); 2.22 (s, 3H); 1.3-2.0 (m, 1H); 1.5 (s, O$\underline{H}$); 1.4 (d, 2H); 1.3 (s, 3H); 0.92 u. 0.90 (2 d, J=7 Hz, Σ 6H). |
| (W) (a) | δ = 8.2-8.35 (m, 1H); 7.7-7.9 (m, 2H); 7.3-7.6 (m, 4H); 3.98 (s, 2H); 3.36 (s, 2H); 2.38 (s, 3H); 2.1 (br, O$\underline{H}$); 1.2-1.9 (m, 6H); 1.56 (s, 3H); 0.95 (ps.t., 3H). |
| (b) | δ = 8.2-8.35 (m, 1H); 7.7-7.9 (m, 2H); 7.3-7.6 (m, 4H); 5.85 (AB-portion of an $ABX_2$-system, 2H); 3.90 (s, 2H); 3.12 (m, 2H); 2.25 (s, 3H); 1.2-1.7 (m, 6H + O$\underline{H}$); 1.28 (s, 3H); 0.9 (ps.t., 3H). |
| (X) (a) | δ = 8.2-8.35 (m, 1H); 7.7-7.9 (m, 2H); 7.3-7.6 (m, 4H); 4.0 (s, 2H); 3.38 (s, 2H); 2.4 (s, 3H) 1.96 (br, O$\underline{H}$); 1.54 (s, 3H); 1.14 (s, 9H). |
| (b) | δ = 8.2-8.4 (m, 1H); 7.65-7.9 (m, 2H); 7.3-7.6 (m, 4H); 5.6-6.1 (AB-portion of an $ABX_2$-system, J=15 + 2x5.5 Hz, 2H); 3.92 (s, 2H); 3.16 (d, 2H; J=5.5 Hz); 2.25 (s, 3H); 1.4 (br, OH); 1.26 (s, 3H); 0.96 (s, 9H). |
| (Y) (a) | δ = 8.2-8.35 (m, 1H); 7.6-7.9 (m, 4H); 7.2-7.6 (m, 7H); 4.0 (s, 2H); 3.4 (s, 2H); 2.65 (br,OH) 2.4 (s, 3H); 1.85 (s, 3H). |
| (b) | 8.15-8.35 (m, 1H); 7.65-7.9 (m, 2H); 7.2-7.6 (m, 9H); 5.6-6.1 (AB-portion of an $ABX_2$-system, J=15 Hz + 2x5.5 Hz, 2H); 3.88 (s, 2H); 3.13 (d, J=5.5 Hz, 2H); 2.24 (s, 3H); 2.0 (s, OH); 1.65 (s, 3H). |

I claim:

1. A compound of the formula:

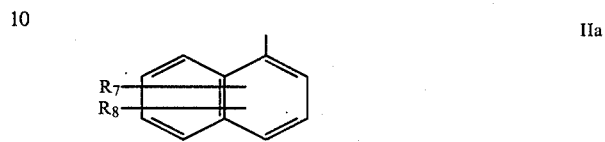

wherein the double bond is in the trans configuration and $R_1$ is a radical of formula IIa,

$R_2$, $R_3$, $R_5$, $R_7$ and $R_8$ are each hydrogen,
$R_4$ is methyl, and
$R_6$ is a radical of formula IIIa $$-C\equiv C-R_{11}$$    IIIa where $R_{11}$ is n-butyl, tertiary butyl or phenyl or a chemotherapeutically acceptable acid addition salt thereof.

2. The trans compound according to claim 1 in which $R_1$ is 1-naphthyl, $R_2$ and $R_3$ are H; $R_4$ is $CH_3$, $R_5$ is H, and $R_6$ is —C≡C—$C_6H_5$.

3. N-Methyl-N-(1-naphthylmethyl)-non-2(trans)en-4-ynyl-1-amine or a chemotherapeutically acceptable acid addition salt thereof.

4. N-Methyl-N-(1-naphthylmethyl)-6,6-dimethyl-hept-2(trans)-en-4-ynyl-1-amine or a chemotherapeutically acceptable acid addition salt thereof.

5. A compound as claimed in claim 1 in the form of its hydrochloride.

6. A chemotherapeutical composition comprising an effective amount of a compound as claimed in claim 1 or a chemotherapeutically acceptable acid addition salt thereof in admixture with a chemotherapeutically acceptable diluent or carrier.

7. A method of treating diseases or infections caused by mycetes which comprises administering to a subject in need of treatment an effective amount of a compound as claimed in claim 1 or a chemotherapeutically acceptable acid addition salt thereof.

* * * * *

UNITED STATES PATENT AND TRADEMARK OFFICE

CERTIFICATE EXTENDING PATENT TERM UNDER 35 U.S.C. § 156

PATENT NO.      :   4,755,534

DATED           :   July 5, 1988

INVENTOR        :   Anton Stuetz

PATENT OWNER    :   Sandoz Pharmaceuticals Corporation

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

543 DAYS from the date of expiration of the original patent term with all rights pertaining thereto as provided by 35 U.S.C. § 156(b).

I have caused the seal of the Patent and Trademark Office to be affixed this 15th day of December 1994.

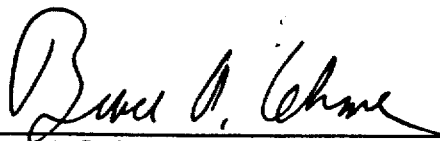

Bruce A. Lehman
Assistant Secretary of Commerce and
Commissioner of Patents and Trademarks